United States Patent
Krumme et al.

(10) Patent No.: US 9,763,960 B2
(45) Date of Patent: Sep. 19, 2017

(54) WAFER COMPRISING STEROID HORMONES

(75) Inventors: Markus Krumme, Randolph, NJ (US); Albert Radlmaier, Oberkrämer (DE); Sascha General, Berlin (DE); Michael Dittgen, Apolda (DE); Keith Jensen, Clifton, NJ (US)

(73) Assignee: LTS Lohmann Theraple-Systeme AG, Andernach (DE)

( * ) Notice: Subject to any disclaimer, the term of this patent is extended or adjusted under 35 U.S.C. 154(b) by 1482 days.

(21) Appl. No.: 11/391,646

(22) Filed: Mar. 28, 2006

(65) Prior Publication Data
US 2006/0222708 A1 Oct. 5, 2006

(30) Foreign Application Priority Data
Mar. 31, 2005 (DE) .................. 10 2005 015 128

(51) Int. Cl.
| A61K 9/22 | (2006.01) |
| A61K 31/57 | (2006.01) |
| A61K 31/56 | (2006.01) |
| A61K 31/568 | (2006.01) |

(52) U.S. Cl.
CPC ............ A61K 31/56 (2013.01); A61K 31/568 (2013.01)

(58) Field of Classification Search
CPC ...... A61K 31/57; A61K 31/365; A61K 9/006; A61K 31/56; A61K 31/568
USPC .......................... 424/454, 435; 514/177, 179
See application file for complete search history.

(56) References Cited

U.S. PATENT DOCUMENTS

| 4,136,162 A | | 1/1979 | Fuchs et al. | |
| 4,764,378 A | * | 8/1988 | Keith et al. | 424/435 |
| 5,780,045 A | * | 7/1998 | McQuinn et al. | 424/434 |
| 5,948,430 A | * | 9/1999 | Zerbe et al. | 424/435 |
| 6,264,981 B1 | | 7/2001 | Zhang et al. | |
| 6,709,671 B2 | * | 3/2004 | Zerbe et al. | 424/435 |
| 2003/0068378 A1 | * | 4/2003 | Chen et al. | 424/486 |
| 2004/0132087 A1 | * | 7/2004 | Meyers et al. | 435/6 |

FOREIGN PATENT DOCUMENTS

| CA | 2265651 | 5/1998 |
| GB | 981372 | 1/1965 |
| WO | WO 02/03965 A1 | 1/2002 |

OTHER PUBLICATIONS

Jay et al. (J of Pharm Sci, vol. 91, 2016-2025).*
Nunez et al. (J of Pharm Sci, 86, 10, 1997, 1187-1189).*
MeSH topical admin—downloaded from www.ncbi.nlm.nih.gov/mesh/68000287 on Feb. 20, 2014.*
Baisley et al, "Pharmacokinetics, Safety and Tolerability of Three Dosage Regimens of Buccal Adhesive Testosterone Tablets in Healthy Men Suppressed with Leuprorelin", Journal of Endocrinology, 2002, 175, 813-819.
Wang et al, "Testosterone Metabolic Clearance and Production Rates Determined by Stable Isotope Dilution/Tandem Mass Spectrometry in Normal Men: Influence of Ethnicity and Age", The Jounal of Clinical Endrocrinology & Metabolism, 89(6), pp. 2936-2941.

* cited by examiner

*Primary Examiner* — Sarah Pihonak
*Assistant Examiner* — Jason A Deck
(74) *Attorney, Agent, or Firm* — Haug Partners LLP

(57) ABSTRACT

The invention relates to a pharmaceutical composition in the form of a system in film form for transmucosal administration of steroid hormones. An administration system for steroid hormones which dissolves in the mouth and which releases with a high bioavailability is disclosed. The administration system in film form dissolves in the mouth preferably in a period of less than 30 min, and the steroid hormone entering the bloodstream transmucosally from the administration system leads to a rapid rise in the concentration in the blood. It is thus possible to achieve a maximum concentration of this steroid hormone in the blood in a period of less than 60 min after administration.

31 Claims, No Drawings

WAFER COMPRISING STEROID HORMONES

The invention relates to a pharmaceutical composition in the form of a system in film form for transmucosal administration of steroid hormones.

Various administration forms of steroid hormones have been described. Besides conventional oral administration, also available are implants, patches and gels. These administration forms aim at continuous delivery of the steroid hormones which is as uniform as possible over a lengthy period. However, for various applications, an administration leading a rapid rise in the concentration of the steroid hormone in the blood would be desirable. In order for example in a case of male testosterone deficiency to restore the physiological state, it would be necessary to achieve a concentration peak in the morning. The prerequisite for this would be a rapid uptake of the hormone and a high bioavailability in order to achieve a high blood concentration in a short time.

Rapid release of active ingredients can be achieved by a transmucosal administration. Dosage forms which disintegrate in an aqueous environment, e.g. in the mouth, are known for this purpose. Buccal administration systems such as patches, suckable tablets, chewing gum, films and melting tablets are known.

Particular mention should be made in this connection of systems in film form, called wafer (U.S. Pat. No. 5,948,430). After application of a wafer in the mouth, the active ingredient is released into the surroundings. To achieve a rapid rise in the concentration of the active ingredient in the blood, it is particularly important that absorption of the active ingredient through the oral mucosa is rapid. Poor solubility or absorption cannot be compensated by enlarging the wafer at will, because the size of the wafer is limited by the size of the mouth, and thick wafers disintegrate only very slowly.

The active pharmaceutical ingredients present in the wafers are absorbed either buccally or sublingually through the oral mucosa, depending on the absorption site. These modes of administration are distinguished by numerous advantages compared with oral administration, such as, for example, avoiding the first-pass effect, faster onset of action, and evading gastrointestinal metabolism.

Muci adhesion plays a key role in the development of a buccal or sublingual administration system. Materials which bind to the mucin layer of biological membranes are normally referred to as "mucoadhesive". Mucoadhesive polymers have been employed many times in numerous administration forms in order to make certain active ingredients systemically bioavailable by administration through various mucous membranes. Such pharmaceutical formulations include tablets, patches, strips, films, semisolids and powders. Polymers must have certain physicochemical properties in order to be mucoadhesive. Thus, such polymers must be predominantly anionic and hydrophilic due to numerous hydrogen-bonding groups, have sufficient wettability on the surface of the mucosal tissue, and have adequate flexibility in order to penetrate through the mucosa or tissue fissure.

A major problem in the development of buccal and sublingual administration systems is, however, the low active ingredient flux rate through the mucosal epithelial tissue, which leads to a low bioavailability of the active ingredient.

The ability of a drug to penetrate into the human oral mucosa depends inter alia on the drug's lipid solubility, which is expressed by the oil/water partition coefficient. This connection has been shown by way of example for carboxylic acids, alkylphenylacetic acids, fatty acids, amphetamines and fenfluramines, acetanilides and steroids.

For steroids, it has been shown that buccal absorption thereof depends in a biexponential function on the oil/water partition coefficient. Log P values between 1.6 and 3.3 are regarded as favorable for sublingual absorption. It has been possible to show for a number of progesterone derivatives that the rate constant for uptake through the mucosa decreases with decreasing log P (increasing hydrophilicity).

Since two parallel routes of buccal absorption exist, it has been postulated that substances with virtually identical solubility in water and oil permeate best. However, this contrasts with the finding that in homologous series the permeation increases with increasing hydrophobicity.

Further parameters for assessing the absorption of active ingredients through the buccal mucosa are physicochemical properties such as the solubility and the rate of dissolution. The solubility of an active ingredient in the medium present in the mouth determines the concentration gradient which describes the diffusion pressure. A high solubility generates a high diffusion pressure. In this connection, the volume of liquid present in the mouth amounts to only a few milliliters.

The steroid hormones described herein show a solubility of 30 μg to a maximum of 1 mg in the volume available. However, the amount of all substances which is required for medical application is distinctly higher than this.

U.S. Pat. No. 6,264,981 describes various possibilities which meet this challenge. U.S. Pat. No. 6,264,981 describes a buffered formulation for weak acids and bases, i.e. ionizable substances. The buffering leads to the substances mentioned therein being in the form of a salt which is ionized and thus more soluble. However, the steroid hormones described herein cannot readily be converted into a salt form.

Various chemical substances have been tested for their utility as penetration and absorption enhancers for transmucosal application, with the tolerability and safety being an important aspect. In the concentration necessary for increasing the mucosal absorption, however, the use of many known permeation enhancers potentially led to irritation and/or damage of the mucosal membranes.

Since permeation enhancers by definition damage the mucosa, the serious disadvantages of enhancing permeation with such permeation enhancers include destruction of the buccal mucosa for example through loss of the upper layers of cells and the decrease in the number of desmosomes, and the irritation of the buccal epithelium by salts, sodium lauryl sulfate or bile acids.

Steroid hormones are lipophilic substances which have only very poor solubility in water. In view of the metabolic clearance of testosterone (C. Wang, D. H. Catlin, B. Starcevic, A. Leung, E. DiStefano, G. Lucas, *J. Clin. Endocrin. Metab.*, 89, 2936-2941, 2004) and the pharmacokinetic data for the testosterone tablet administered buccally to men, the value calculated for the bioavailability of the buccal-adhesive testosterone tablet is of the order of 25% (K. J. Baisley, M. J. Boyce, S. Bukofzer, R. Pradhan, S. J. Warrington, *J. Endocrin.* 175, 813-819, 2002).

Since administration systems in film form for buccal application are limited both in the area and in the thickness, a bioavailability of 25% is inadequate for some steroids. The area of the wafer is limited by the free buccal area, which is about 7 cm$^2$ per side. If the wafer becomes larger, uniform and safe administration can be ensured only with reduced reliability. It is also not readily possible by increasing the loading of the wafers or by excessive "thickening" of the wafer to achieve a higher concentration of dissolved active ingredient at the absorption site (buccal mucosa), because the risk of unwanted swallowing of the active ingredient due to newly formed saliva is increased thereby.

Very fast and high absorption is therefore reliant on films which dissolve, and thus make available for absorption through the buccal mucosa, both the carrier material and the active ingredient in a very short time (preferably within less than 15 minutes). Nor does the use of a sequence of buccally applied films with low availabilities serve the purpose of a fast onset of action. Restoration of the conditions in the mouth as before use of the first film within such a series would require complete replacement of the available saliva. In addition, complete absorption or removal of the previous wafer must be guaranteed in order to ensure constant and thus reproducible absorption. These requirements would result in a time interval of at least 30 min between the applications of two wafers.

The solubility of steroid hormones, which are not ionizable in physiological pH ranges and have inadequate solubility, with a log P of 1.0-4.3, cannot for the same absorption be improved by the other measures described in U.S. Pat. No. 6,264,981 (cyclodextrins, inclusion compounds) either.

The rate of dissolution of carrier material and active ingredient is of great importance especially for use in the mouth because there is continuous formation of about 0.5-3 ml/min fresh saliva there. This is subsequently conveyed, in a manner not controllable by the user, by swallowing into the gastrointestinal tract. The active ingredient is subject there, as on oral administration, to the disadvantages of slow uptake and the metabolic first-pass effect.

The object of the present invention was therefore to provide an administration system which dissolves in the mouth for steroid hormones which are not ionizable at physiological pH values and have a log P of 1.0-4.3, preferably without addition of permeation enhancers, which releases the steroid hormones contained therein with a high bioavailability, preferably greater than 50%, with the maximum blood level (=maximum concentration) of the steroid hormone contained therein being reached within 60 minutes.

The object on which the present invention is based has been achieved through the provision of an administration system which dissolves in the mouth and which comprises 0.01 to 50% by weight, preferably 2-15% by weight, of at least one steroid hormone and 50-99.99% by weight, preferably 80-98% by weight, of a carrier material. Suitable carrier materials are in particular cellulose and derivatives thereof, such as methylcellulose, ethylcellulose, hydroxypropyl-cellulose, hydroxyethylcellulose, hydroxypropylmethyl-cellulose (HPMC), and poly-N-vinylpyrrolidones, vinyl-pyrrolidone-vinyl acetate copolymers, starch, starch derivatives, gelatin, gelatin derivatives and combinations thereof.

A preferred administration system comprises 2-15% by weight, particularly preferably 3-8% by weight, of a steroid hormone—especially of an androgen—and 80-98% by weight of a carrier material—especially a cellulose derivative.

A particularly preferred administration system comprises 5% by weight of a steroid hormone from the group consisting of testosterone, 7α-methyl-19-nortestosterone and 7α-methyl-11β-fluoro-19-nortestosterone and 95% by weight of hydroxypropylmethylcellulose (HPMC).

It is preferred according to the present invention for the administration systems which dissolve in the mouth to be in film form. These administration systems in film form are also referred to as "wafers". The inventive administration systems in film form can, in a particular embodiment, be endowed with mucoadhesion. By this is meant the property of adhering to a mucous membrane, specifically in such a manner that it is impossible to detach the administration system from the mucous membrane subsequent to the application.

The administration systems in film form of the present invention have an area of between 1 and 10 $cm^2$, preferably between 5 and 8 $cm^2$ and particularly preferably of 7 $cm^2$. They moreover have a weight per unit area of between 50 and 250 $g/m^2$, preferably between 100 and 150 $g/m^2$. The latter approximately correlates with a thickness of between 40 and 130 µm, preferably between 50 and 100 µm.

The administration system in film form dissolves in the mouth preferably in a period of less than 30 min, particularly preferably in a period of less than 15 min. The steroid hormone which enters the bloodstream transmucosally from the administration system leads to a rapid rise in the concentration of this steroid hormone in the blood. In this case, a maximum concentration of this steroid hormone in the blood is reached preferably in a period of less than 60 min—particularly preferably in a period of between 15 and 30 min—after application.

The high bioavailability of the steroid hormone and the ability to achieve a pulsatile course of the hormone concentration in the blood, with a marked decline, is characteristic of the inventive administration system. The administration system thus makes possible pulsatile, circadian or the like hormone therapy adapted to the natural rhythm.

It is possible with the administration system to achieve a bioavailability of at least 25%, preferably of at least 50%, of the steroid hormones. In a particularly preferred embodiment, the steroid hormone is released with a bioavailability of between 70 and 75%.

The administration system in film form may, besides the carrier material and the steroid hormone, comprise further substances, for example flavorings, colorants, permeation enhancers, sweeteners, fillers, liquid—preferably lipophilic—excipients which are able to dissolve the steroid hormone and form a second phase in the—preferably hydrophilic—carrier material, solubilizers, pH stabilizers, disintegrants. In a preferred embodiment, the administration system is free of penetration enhancers, absorption enhancers and/or permeation enhancers.

The administration system is preferably employed for pulsatile treatment in the circadian rhythm. A pulsatile release of the drug generally makes possible a better (chronopharmaceutical) treatment of diseases with an oscillatory rhythm in their pathogenesis, such as asthma; arthritis, small bowel cancer and other cancers, diabetes, cardiovascular disorders, gall bladder disorders and neurological disorders.

The administration system is particularly preferably used as part of a therapy in which an elevated concentration of a steroid hormone in the blood is achieved in a short time, preferably in a period of less than 60 min, by means of once daily administration. The administration system can be administered in particular as part of an androgen therapy once in the morning in order to achieve an elevated blood concentration of the administered androgen in a short time.

Steroid hormones according to the present invention may be estrogens, progesterones, androgens and corticosteroids having a log P of 1.0-4.3.

The preferred estrogen is ethinylestradiol. Preferred progesterones are drospirenone, dienogest, gestodene, levonorgestrel, cyproterone acetate.

Corticosteroids suitable for the purposes of the present invention are hydrocortisone, hydrocortisone 21-acetate, methylprednisolone aceponate, prednisolone, deflazacort, deflazacort alcohol, fluocortolone and fluocortolone hydrate, fluocortolone 21-pivalate.

Androgens suitable for the purposes of the present invention are testosterone, dihydrotestosterone, 7α-methyl-19-nortestosterone (MENT), MENT 17-acetate, 7α-methyl-11β-fluoro-19-nortestosterone (eF-MENT), mesterolone, metenolone, nandrolone, oxandrolone, androstenedione.

All the examples fall within the log P range of 1.0-4.3.

Administration systems comprising the androgen MENT or eF-MENT are preferred according to the present invention.

Administration systems which comprise 95% HPMC and 5% MENT or eF-MENT are particularly preferred.

The following examples illustrate the production of suitable administration systems ("wafers"). The compositions of the dried wafers are represented in table 1.

EXAMPLE 1

5 g of MENT are added to 700 ml of an ethanol/water (50:50) solution and stirred until dissolution is complete. The dissolution is assisted where appropriate by application of ultrasound. 95 g of hydroxypropylmethylcellulose (HPMC) are then added, and the mixture is stirred until dissolution is complete.

The mixture is degassed, spread out with the aid of a spreading box and dried. A thin transparent film which is between 50 and 100 μm thick is produced. Transparent wafers with a content of 1.5 mg of MENT are obtained by cutting out samples of appropriate size.

EXAMPLE 2

3 g of menthol and 2 g of thymol are added to 26 g of ATMOS 300 (=a mixture of mono- and diglycerides of oleic acid) and 4 g of Tween 80 (=a polyoxyethylene sorbitan oleate ester). The mixture is stirred until the solids have dissolved. Then 5 g of MENT are added to this mixture, which is stirred until the active ingredient has completely dissolved. 60 g of HPMC are added to 600 g of a 50:50 ethanol-water mixture and stirred until dissolution is complete. The organic phase is then added slowly and with high-speed stirring to the aqueous phase, resulting in a thick, creamy composition. Degassing of the mixture and spreading out are followed by drying. A thin translucent film which is between 50 and 100 μm thick is produced. Translucent wafers with a content of 1.5 mg of MENT are obtained by cutting out samples of appropriate size.

EXAMPLE 3

5 g of MENT are added to a mixture of 20 g of ATMOS 300, 10 g of octanol and 5 g of lecithin. The mixture is stirred until the solids have dissolved. 60 g of HPMC are added to 600 g of water and stirred until dissolved. The organic phase is added with high-speed stirring to the aqueous phase, resulting in a thick creamy composition. Degassing of the mixture and spreading out are followed by drying. A thin translucent film which is between 50 and 100 μm thick is produced. Translucent wafers with a content of 1.5 mg of MENT are obtained by cutting out samples of appropriate size.

TABLE 1

Compositions of dried MENT wafers

| Example | MENT (%) | HPMC (%) | ATMOS 300 (%) | Tween 80 (%) | Octanol (%) | Lecithin (%) | Menthol (%) | Thymol (%) |
|---|---|---|---|---|---|---|---|---|
| 1 | 5 | 95 | — | — | — | — | — | — |
| 2 | 5 | 60 | 26 | 4 | — | — | 3 | 2 |
| 3 | 5 | 60 | 20 | — | 10 | 5 | — | — |

It may be noted that the dried systems of example 1 comprise the steroid hormone dissolved as a mono-molecular dispersion in the carrier material, whereas the steroid hormone in examples 2 and 3 is in the form of a solution in an oil phase which is in turn present in the carrier material as separate phase. The use of liquid, preferably lipophilic excipients which are able to dissolve the steroid hormone and to form a second phase in the (preferably hydrophilic) carrier material thus makes it possible to produce administration systems in film form with steroid hormones as "two-phase system".

Experimental Data

A clinical pilot study was performed on healthy men to test whether a MENT wafer is suitable in principle for clinical use. Essential aspects of the trial related to the levels of active ingredient which can be achieved in the blood by the wafer and the time course thereof, and the general tolerability. Three different dosages of the wafer were tested. Each subject received all three dosages each as a single administration in a crossover design. There was a washout period of at least 48 hours between the individual administrations.

The three dosages were fixed so that there was a realistic possibility of being able to measure blood levels of MENT with the available methods of measurement, even if the bioavailability was very low, at least at the high dose level and, on the other hand, if the bioavailability is very high the theoretically conceivable peak levels are still within the safety range proven by clinical or preclinical data.

The dose groups were 0.5 mg, 1.5 mg and 3.0 mg. The level of the dosage was determined by the size of the wafer. The wafer used comprised 0.225 mg of MENT/1 cm$^2$. The single administration took place in a dose of 0.5 mg with a wafer having an area of 2.22 cm$^2$ (formulation a), for 1.5 mg with a wafer having an area of 6.67 cm$^2$ (formulation b), and for 3.0 mg with two wafers each of 6.67 cm$^2$. The wafers were applied to the buccal mucosa by the clinical investigator. The low dose was always introduced on the right-hand side, the middle dose always on the left-hand side, and for the high dose one wafer was used on each side.

Both C-max and the AUC show a clear dose-linearity. The highest concentrations are measured within 15 to 30 minutes and then fall rapidly; only insignificant concentrations are measurable after more than 4 hours.

The serum levels of MENT were determined by employing a GC-MS method (coupled gas chromatography-mass spectrometry) (specifically developed and validated for this purpose). The method makes use of the process of negative chemical ionization (NCI) and thus achieves high sensitivity permitting concentrations to be measured down to a lower limit of approximately 60 pg/ml (lower limit of quantification).

A GC-MS method is also available for measurements of lower sensitivity, which employs the process of electron ionization (EI) instead of NCI.

In principle, the MENT concentration can also be determined by other methods which are otherwise suitable for determining steroid hormones. Suitable examples which may be mentioned without a claim to completeness are radioimmunoassays, LC-MS techniques, or HPLC methods (high performance liquid chromatography).

TABLE 3

Overview of characteristic pharmacokinetic data of the tested dosages of the MENT wafer

| Treatment | Formulation | Dose (mg) | Cmax geomean (CV) [ng/ml] | Tmax median (range) [h] | AUC (0-tlast) geomean (CV) [ng × h/ml] |
|---|---|---|---|---|---|
| A | a | 0.50 | 3.29 (67.8%) | 0.25 (0.25–2.00) | 3.78 (44.5%) |
| B | b | 1.50 | 8.98 (39.4%) | 0.50 (0.25–0.75) | 11.0 (17.8%) |
| C | b | 3.00 | 18.2 (31.2%) | 0.50 (0.25–0.75) | 21.1 (16.2%) |

CV = coefficient of variation

In total, 11 men between 23 and 42 years of age received the wafer without relevant side effects being observed. The local tolerability was very good. Visual inspection of the application site revealed no signs of unwanted local reactions. The subjects used a visual analog scale to represent their subjective impression of the local tolerability. There was no evidence of relevant unwanted effects here either.

The wafer had dissolved within 15 minutes for the majority of uses. It took longer in some cases; the maximum time in one case was 33 minutes. The available data support the assumption that the bioavailability is lower when the time taken for the wafer to dissolve is distinctly prolonged.

The MENT wafer showed a surprisingly good bioavailability of about 70-75% (Tab. 2).

The available clinical results with MENT indicate that serum concentrations of at least 0.3 ng/ml (about 1 nmol/l) are necessary for effective prevention of hypogonadal symptoms in men. This is about 10-times lower than the minimum concentration of testosterone.

The MENT wafer system achieves these serum levels without difficulty. With the pharmacokinetics found, the MENT wafer approaches an intravenous administration. Because of the short half-life, use of the wafer is worthwhile when a brief but very efficient rise in the androgen level is desirable. "Brief" for this indication is to be regarded as a period of less than 60 min, preferably between 15 and 30 min.

One advantage of the application, which is restricted to the acute case of need, is to be regarded as being that the inhibitory effect on testicular function is only slight and a

TABLE 2

Bioavailability of the MENT wafer

| Treatment | Formulation | Dose (mg) | AUC(0-tlast) geomean [ng × h/ml] | AUC(0-tlast) geomean dose-normalized [ng × h/ml] | AUC(0-tlast) geomean dose-normalized [ng × h/ml] | Bioavailability [%] |
|---|---|---|---|---|---|---|
| A | a | 0.50 | 3.78 | 3.78 | | 75.9 |
| B | b | 1.50 | 11.00 | 3.67 | 4.98 (after i.v. admin. of 0.5 mg MENT) | 73.6 |
| C | b | 3.00 | 21.10 | 3.52 | | 70.6 |

The interindividual variation in the AUC is below 20% which is to be categorized as low.

negligible impairment of the corresponding physiological functions is to be expected. In contrast to androgen products with longer activity, therefore, neither impairment of the available gonadal testosterone synthesis nor inhibition of spermatogenesis is to be expected on use of the inventive administration system with an androgen as active ingredient.

One suitable area of use of the inventive administration system from the area of androgens is therefore administration once a day to restore the circadian androgen rhythmicity in elderly men. The age-associated reduction in the endogenous testosterone concentration in men is characterized in particular by loss of the circadian rhythmicity. The rise in testosterone levels to be observed in the morning substantially disappears. Thus, the largest difference in testosterone levels between young and old men is detectable in blood samples taken in the morning, whereas there are only small differences when taken in the evening. It is possible with the aid of the inventive administration system to treat the age-related relative androgen deficiency in accordance with the androgen rhythmicity, with scarcely any impairment in practice of the available endogenous testosterone production. In these cases, self-treatment of the patient is possible easily and conveniently in an advantageous manner.

The invention claimed is:

1. An administration system in film form for transmucosal administration of a steroid hormone, comprising:
   0.01-50% by weight of a steroid hormone which is selected from the group consisting of an estrogen, a progesterone, an androgen, and a mixture thereof;
   50-99.99% by weight of a carrier material, selected from the group consisting of cellulose, cellulose derivatives, poly-N-vinylpyrrolidones, vinylpyrrolidone-vinyl acetate copolymers, starch, starch derivatives, gelatin, gelatin derivatives and combinations thereof;
   wherein the steroid hormone is dissolved in the carrier material; and
   wherein the administration system:
      has a weight per unit area of between 50 and 250 g/m$^2$;
      has a thickness of between 40 and 130 μm;
      dissolves in the mouth completely in a period of less than 30 minutes; and
      releases the steroid hormone contained therein on buccal administration with a bioavailability of at least 50%.

2. The administration system as claimed in claim 1;
   wherein the carrier material is methylcellulose, ethylcellulose, hydroxypropylcellulose, hydroxyethylcellulose, hydroxypropylmethylcellulose (HPMC) or a combination thereof.

3. The administration system as claimed in claim 1;
   wherein the carrier material is hydroxypropylmethylcellulose (HPMC).

4. The administration system as claimed in claim 1, further comprising:
   liquid excipients which are able to dissolve the steroid hormone and to form a second phase in the carrier material.

5. The administration system as claimed claim 4;
   wherein the steroid hormone is present dissolved in the liquid excipient.

6. The administration system as claimed in claim 1;
   wherein the steroid hormone is present in an amount of from 2 to 15% by weight.

7. The administration system as claimed in claim 1;
   wherein the administration system has an area of between 1 and 10 cm$^2$.

8. The administration system as claimed in claim 1;
   wherein the administration system has a weight per unit area of between 100 and 150 g/m$^2$.

9. The administration system as claimed in claim 1;
   wherein the administration system has a thickness of between 50 and 100 μm.

10. The administration system as claimed in claim 1;
    wherein the administration system is mucoadhesive.

11. The administration system as claimed in claim 1;
    wherein the androgen is selected from the group consisting of testosterone, dihydrotestosterone, 7α-methyl-19-nortestosterone (MENT), MENT 17-acetate, 7α-methyl-11β-fluoro-19-nortestosterone (eF-MENT), mesterolone, metenolone, nandrolone, oxandrolone, androstenedione, and mixtures thereof.

12. The administration system as claimed in claim 1;
    wherein the steroid hormone is 7α-methyl-19-nortestosterone (MENT) or 7α-methyl-11β-fluoro-19-nortestosterone (eF-MENT).

13. The administration system as claimed in claim 1, further comprising:
    at least one excipient selected from the group consisting of flavorings, colorants, permeation enhancers, sweeteners, fillers, plasticizers, solubilizers, pH stabilizers, and disintegrants.

14. The administration system as claimed in claim 1;
    wherein the administration system releases the steroid hormone contained therein on buccal application with a bioavailability of between 70 and 75%.

15. A method for the treatment of disorders and/or dysfunctions attributable to a steroid hormone deficiency, comprising:
    administering a steroid hormone by the application of the administration system of claim 1 to a patient in need thereof.

16. The method as claimed in claim 15,
    wherein the steroid hormone is administered transmucosally.

17. The method as claimed in claim 15;
    wherein the disorder and/or dysfunction attributable to a steroid hormone deficiency is an androgen deficiency.

18. The method as claimed in claim 15;
    wherein the steroid hormone reaches a maximum blood concentration in a period of less than 60 min after administration of the medicament.

19. The method as claimed in claim 18;
    wherein the steroid hormone reaches a maximum blood concentration in a period of less than 30 min after administration of the medicament.

20. A process for producing an administration system in film form of claim 1 for transmucosal administration of a steroid hormone, comprising:
    mixing the steroid hormone in the form of a solution in a pharmaceutically acceptable solvent with a water-containing mixture of a carrier material;
    spreading out the mixture produced by the mixing step as a thin layer, and
    drying the thin layer by removing the solvent to form a film.

21. The process as claimed in claim 20;
    wherein the resulting film is divided into individual administration systems by perforation, cutting transversely, and/or cutting longitudinally.

22. A method for the treatment of disorders and/or dysfunctions attributable to a steroid hormone deficiency, comprising:
    a first step of applying the administration system of claim 1, which comprises at least one steroid hormone, to the mucosa in the mouth; and a second step where the at least one steroid hormone penetrates transmucosally into the bloodstream.

23. The method as claimed in claim 22;
wherein the steroid hormone penetrates into the bloodstream in a period of less than 30 min after application of the administration system to the mucosa in the mouth.

24. The administration system as claimed in claim 2;
wherein the system comprises:
   (1) between 3 and 8% by weight of a steroid hormone;
   (2) has an area of between 5 and 8 cm$^2$;
   (3) has a weight per unit area of between 100 to 150 g/m$^2$; and
   (4) has a thickness of between 50 and 100 μm.

25. The administration system as claimed in claim 3;
wherein the system comprises:
   (1) between 3 and 8% by weight of a steroid hormone;
   (2) has an area of between 5 and 8 cm$^2$;
   (3) has a weight per unit area of between 100 to 150 g/m$^2$; and
   (4) has a thickness of between 50 and 100 μm.

26. The administration system as claimed in claim 24;
wherein the steroid hormone is 7α-methyl-19-nortestosterone (MENT) or 7α-methyl-11β-fluoro-19-nortestosterone (eF-MENT).

27. The administration system as claimed in claim 25;
wherein the steroid hormone is 7α-methyl-19-nortestosterone (MENT) or 7α-methyl-11β-fluoro-19-nortestosterone (eF-MENT).

28. The administration system as claimed in claim 26;
wherein the administration system releases the steroid hormone contained therein on buccal application with a bioavailability of between 70 and 75%.

29. The administration system as claimed in claim 27;
wherein the administration system releases the steroid hormone contained therein on buccal application with a bioavailability of between 70 and 75%.

30. The administration system as claimed in claim 1;
wherein the estrogen is ethinylestradiol.

31. The administration system as claimed in claim 1;
characterized in that wherein the progesterone is selected from the group consisting of drospirenone, dienogest, gestodene, levonorgestrel, cyproterone acetate, and mixtures thereof.

\* \* \* \* \*